US006054082A

United States Patent [19]

Heide et al.

[11] Patent Number: 6,054,082

[45] Date of Patent: Apr. 25, 2000

[54] SOLIDIFIED DRUG SUPPLY FOR GENERATING INHALABLE DRUG PARTICLES

[75] Inventors: Helmut Heide, Kelkheim; Joachim Pabst, Reinhelm; Hans Burgschat, Mainz, all of Germany

[73] Assignee: GGU Gesellschaft für Gesundheits- und Umweltforschung mbH & Co. Vertriebs KG, Frankfurt, Germany

[21] Appl. No.: 08/817,285

[22] PCT Filed: Oct. 15, 1995

[86] PCT No.: PCT/EP95/04049

§ 371 Date: Apr. 14, 1997

§ 102(e) Date: Apr. 14, 1997

[87] PCT Pub. No.: WO96/11795

PCT Pub. Date: Apr. 25, 1996

[30] Foreign Application Priority Data

Oct. 15, 1994 [DE] Germany ............................ 44 36 854

[51] Int. Cl.[7] ............................ B30B 11/00; B30B 15/02; A61J 3/10

[52] U.S. Cl. .................... 264/109; 264/314; 128/203.15; 128/203.21; 424/464; 425/405.1; 425/405.2

[58] Field of Search .................................... 264/109, 122, 264/314, 325, 319, 315, 320; 425/405.1, 405.2; 128/203.15, 203.21; 424/464

[56] References Cited

U.S. PATENT DOCUMENTS

| | | |
|---|---|---|
| 4,370,120 | 1/1983 | Foster . |
| 5,176,132 | 1/1993 | Drought et al. . |

FOREIGN PATENT DOCUMENTS

| | | |
|---|---|---|
| 1 562 890 | 4/1969 | France . |
| 2 273 206 | 12/1975 | France . |
| 94 00291 | 1/1994 | WIPO . |

*Primary Examiner*—Mathieu D. Vargot
*Attorney, Agent, or Firm*—Henry M. Feiereisen

[57] ABSTRACT

A solidified drug supply for generating inhalable drug particles with the aid of a metering device includes a removal unit, with the drug supply being brittle and textureless. The density and the mechanical strength of the drug supply is abraded everywhere in such a way that the structure of the material removed from one side of the drug supply by the metering device is uniform across the entire usage region in the direction of the removal.

15 Claims, 1 Drawing Sheet

SOLIDIFIED DRUG SUPPLY FOR GENERATING INHALABLE DRUG PARTICLES

BACKGROUND OF THE INVENTION

The present invention relates to a solidified drug supply for generating inhalable drug particles with the aid of a metering device comprising removal means.

Drug supplies of this type are known from WO 93/24165 and are used in aerosol generators having a metering device which includes removal means, for example, in the form of a driven face cutter, for removing drug particles from the drug supply and generating an aerosol which is released for oral or nasal inhalation at the instant when it is generated.

From DE 40 27 390 A1 there is known an inhalation device wherein a brush is used to remove dust-like particles from a tablet wherein the geometrical form of the tablet may vary.

EP 040702882 also describes an aerosol generator having a pressed body of an inhalable drug. The pressure suggested for pressing the drug supply is a so-called lightly densified pressure range between $1\times10^4$ to $15\times10^4$ N/m$^2$ as well as a strongly densified pressure range between $30\times10^4$ and $150\times10^4$ N/m$^2$. However, even this higher pressure range is set to such a low value that the manageable structure can only exist because the drug supply is pressed into a cylindrical container and is held together by that container. Since the drug supply is not compacted very densely, a homogeneous pressure distribution in the bulk of the drug material is not achieved because of the internal friction effects in the bulk and because of the friction between the drug supply and the container wall. As a result, drug supplies of this type exhibit density gradients of more than 40% which have a negative effect on the metering accuracy (see also: B. Chariton and J. M. Newton, "Application of Gamma Ray Attenuation to the Determination of Density Distribution within Compacted Powders", *Powder Technology* 41 (1985), 123 to 134).

Since according to a publication of the applicant of EP 0 407 028 A2, the densities of the drug supply are about 0.8 to 0.9 g/cm$^{-3}$, the volume density for the densified drug supply is calculated to be about 50% of the theoretical density. Accordingly, such a highly porous drug supply is not only very porous and inhomogeneous, but is, as a result of the large open porosity, also subjected to agglomeration and to aging caused by the atmospheric factors, such as humidity and the like.

A solidified drug supply is known from PCT/EP 93/00158, wherein the significance of structural and chemical homogeneity of the solidified drug supply for the metering accuracy pointed out. Therein, isostatic pressing is proposed for obtaining a proper structure; this pressing (molding) method is known from powder metallurgy when flexible forms are employed. Herein, a batch of powder disposed, for instance, inside a rubber form, is densified all around and therefore isostatically from the outside with the help of a pressure liquid. Also proposed in this publication are other forming methods aside from isostatic pressing, for example, injection molding of plastified materials.

Further investigations on solidified drug supplies have shown that the quality requirements with respect to structure are much higher than have been assumed previously. It has been found that during removal by a metering device comprising a removal means, such as known from WO 93/24165, potential variations in density can have a significant effect on the generated amount of aerosol.

It was also observed that isostatically pressed drug supplies initially exhibit inexplicable dose variations at the removal end face, which could not be explained by density or material inhomogeneities measured in the bulk. A more accurate investigation of these occurrences has demonstrated that defects in material, such as texturing and micro-fissures, occur in these marginal regions whereby larger sections of material may chip off during removal, resulting in dosage variations.

It now appears that such defects in material are the result of the isostatic pressing process. Strictly speaking, an ideal isostatic pressure transmission to the powder material occurs only in forms of spherical or nearly spherical geometry. If, however, the shape of the form deviates from the isometric form which is, for example, the case for ring-shaped removal members for inhalation purposes, then the pressure transmission is no longer completely isostatic, but is directional. If, for example, such ring-shaped tablet for an inhalator is isostatically pressed, then radial and axial forces are superposed in the region of the end faces, wherein these forces cause texturing in the critical regions of the end faces, in particular, since a form with this shape exhibits a different stiffness with respect to the hydrostatic pressure and consequently a different deformability when the pressure is building up. This causes an initial densification phase in radial direction and a subsequent post-densification of the already pre-solidified powder material in axial direction which causes the aforementioned textures and micro-fissures in the structure of the ring-shaped tablet. For the known applications of isostatic molding (pressing) in the field of powder metallurgy and ceramics, such developments usually are not important, since the resulting structural defects are annealed during the subsequent sintering process without leaving any blemishes. This possibility however, does not exist with a drug supply which is used without such post-treatment.

It has been found that the above-mentioned friction effects inside a bulk powder material also occur when a drug supply is isostatically pressed, however, not to such extent as with unidirectional pressing methods. Even for an isostatic pressing operation, the pressure loss inside the bulk powder increases with the thickness of the form in the direction facing the pressing force. Consequently, density gradients within the cylinder walls in radial and axial direction occur also during isostatic pressing of a ring tablet, resulting in completely formed zone of equal densities or textures, respectively, in the region of the end face.

SUMMARY OF THE INVENTION

It is the object of the invention to provide a solidified drug supply which can be removed reproducibly over the entire usage region and which produces the desired particle uniformity.

The object of the invention is solved by a drug supply including a solidified body of medicament having a texture formed by applying a pressing force from outside in a direction toward a core positioned centrally in the solidified body. In particular, the solidified body has a density and a mechanical strength is and so defined as to enable an abrasion everywhere in such a way that the structure of the material removed from one side of the drug supply by the metering device is uniform across the entire usage region in the direction of the removal.

The drug supply provided according to the invention may be disposed in an aerosol generator, like aerosol generator known from WO 93/24165 by the present applicant. The device described in this publication is explicitly referenced herein, and is incorporated into the present application by reference. When the aerosol dose is removed by the face cutter operating in an axial direction, the drug supply of the invention provides a very small, but particularly coaxial density distribution which does not affect the generated amount of aerosol and the quantity of the aerosol.

In a preferred embodiment of the invention, the structure of the drug supply may be generated by applying a pressing force in a direction essentially perpendicular to the direction of the subsequent removal. Surprisingly, this method of applying pressure—which is different from isostatic pressing—results in excellent properties of the solidified drug supply. Since in this embodiment the pressing force is applied exclusively in one direction, for example, radially, the density gradient in the drug supply which is generated in this fashion, is also directed strictly radially due to the internal friction described above, i.e. the zones of equal density extend parallel and concentrically to the longitudinal axis of the drug supply.

According to another embodiment of the invention, the drug supply may have a circular cross section and may be fabricated by applying the pressing.

The invention is particularly advantageous with ring-shaped tablets. Here too, a pressing force is essentially directed radially against a stationary core.

As a result of this geometrical shape, a particularly advantageous structure with minimum density gradients in radial and axial direction is attained when only the radial pressing force is applied. According to another preferred embodiment of the invention, the density gradient perpendicular to the removal direction may be no larger than 0.3% and 0.05% in the removal direction. It has not been possible until now to realize such small density gradients with drug supplies adapted for generating inhalable drug particles with a metering device. The drug supply may be fabricated from a granulated carrier material-active ingredient mixture, wherein the pressing forces for the drug supply of the invention are between 50 and 500 MPa.

Another feature of the invention relates to a method for fabricating a solidified drug supply for generating inhalable drug particles with a metering device comprising removal means wherein a pressing force is applied to the drug material. According to the invention, the pressing force is here applied essentially in the direction perpendicular to the direction of the subsequent removal wherein, according to a preferred embodiment, the pressing force in every direction perpendicular to the subsequent removal direction is identical. With this fabrication method, the advantageous properties of an abovedescribed drug supply used for generating drug particles are attained.

Depending on the shape desired for the solidified drug supply, the drug supply is pre-shaped when subjected to the pressing force. For a ring tablet, the drug material—either in powder form or pre-densified—is placed around a stationary core and subsequently pressed against the core by radial pressing force. The core is preferably removed after the pressing step and the ring tablet is taken out.

According to another preferred embodiment of the method, the drug supply is initially formed as a rod-shaped body with, for example, a length of 200 mm, and is subsequently separated perpendicular to its long axis. This method enables a particularly efficient fabrication of the plurality of drug supplies with the desired properties for use in a cooperating aerosol generator.

Another feature of the invention relates to an apparatus for fabricating a solidified drug supply by applying a pressing force to a drug material. The apparatus of the invention comprises a press space formed by at least two parallel stationary plates separated in space and a flexible ram, wherein the faces of the plates and the ram facing the press space are arranged perpendicular with respect to each other. Such apparatus enables the fabrication of a drug supply with the desired properties in an easy and convenient manner.

According to a preferred embodiment, the press space may be a ring space formed about a cylindrical core, the ring space surrounded by the flexible ram, wherein the extrusion die, when subjected to pressure, is moveable towards the core, thereby providing the exclusively radial pressing force.

BRIEF DESCRIPTION OF THE DRAWING

The invention will be described hereinafter with reference to the appended drawing, taking a preferred embodiment as an example. It is shown in.

DETAILED DESCRIPTION OF PREFERRED EMBODIMENTS

Figure 1:
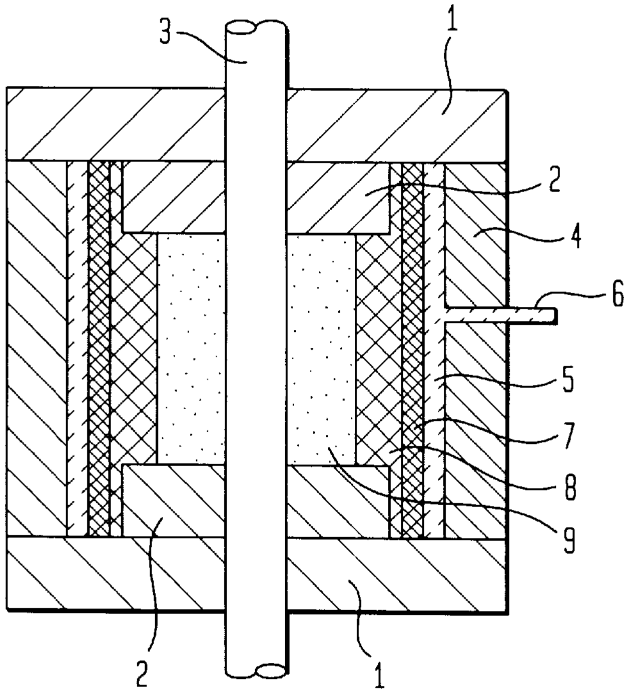
FIG. 1 a schematic cross-sectional view of an apparatus for fabricating a solidified drug supply without applied pressing force.

The press depicted in FIG. 1 for fabricating a solidified drug supply by applying a pressing force to the drug material 9 comprises a press space formed by two parallel stationary and spaced apart plates 2 and a flexible ram 8. The faces of the plates 2 and the ram 8 facing the press space are arranged perpendicular with respect to each other. The outer housing of the press chamber depicted in FIG. 1 is formed by an upper housing plate and a lower housing plate 1 which is pressed firmly onto the ring jacket 4 by the closing force of a hydraulic press (not shown). The closing force of the hydraulic press is significantly higher than the oil pressure acting on the ram inside the press chamber so that the hydraulic liquid cannot leak out. A steel core 3 extends through the center of the two housing plates as well as through the plates 2 and the press space.

As shown in FIG. 1, the flexible ram 8 coaxially surrounds the ring space which is bound on the upper and lower side by the plates 2. The flexible ram 8 extends in length between the two parallel plates 2. The ram 8 is also coaxially surrounded by a flexible pressure membrane 7 which extends axially between the upper and the lower housing plates 1, thereby providing a seal against the pressure medium 5, for example hydraulic oil, which is supplied externally via a connection 6.

For fabricating the solidified drug supply, initially the drug material which may be a granulated carrier/active ingredient mixture made pourable by spray granulation or dry force mixing, is introduced into the press space. After introduction of the drug material into the press space, oil pressure is applied to the press (cf. direction of arrow in FIG. 1*a*), whereby the state shown in FIG. 1*a* is established.

Figure 1A:
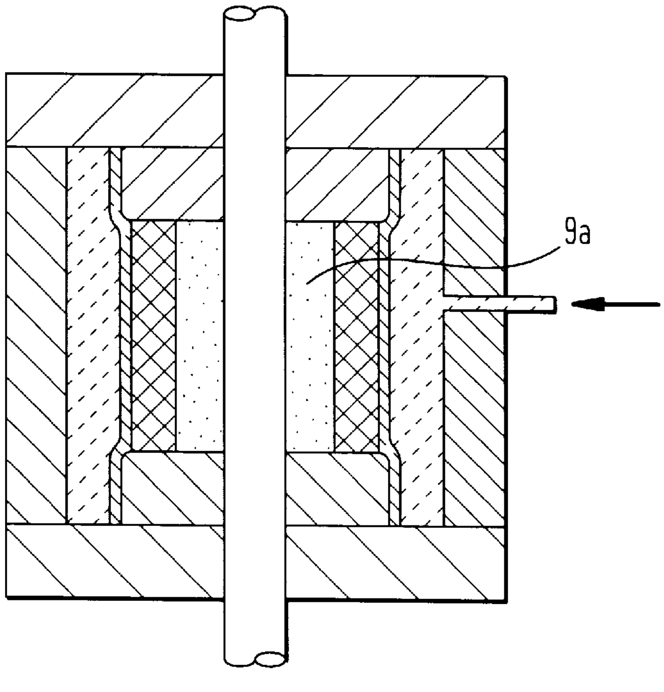
FIG. 1*a* the apparatus of FIG. 1 with pressing force applied.

As is evident from FIG. 1*a*, the plates 2 do not travel during the extrusion process and therefore do not apply an active pressing force to the drug material. To the contrary, they absorb the pressing force applied radially by the hydraulic media 5 via the pressure membrane 7 and the ram 8. By applying the hydraulic pressure concentrically in a radial direction in the direction towards the core 3, the drug material is densified and a solidified drug supply is generated. During the pressing operation, the ram slides slightly radially inwardly on the end faces of the upper and lower plate 2, causing the pressing force to the drug supply 9*a* to be transmitted exclusively radially and thus eliminating any axial shear movement within the drug supply.

A drug supply created in this fashion has, as a result of the abovedescribed internal friction, a density gradient with an exclusively radial orientation, i.e., zones of equal density are arranged parallel and concentrically around the center axis of the drug supply 9*a*.

At the end of the pressing operation, the oil pressure is lowered, the ram 8 and the pressure membrane 7 return to their initial position (FIG. 1), and the drug supply shaped in form of a ring tablet 9*a* is removed after the mold is opened. Technical details of the press chamber, such as sealing of the oil charge and the like, are not shown for the sake of clarity.

The ring-shaped drug supply described above may, for example, have an outside diameter of 16 mm, an inside diameter of 10 mm, and a height of 6 to 60 mm. The drug material may be, for example, a mixture of 7.5% salbutamol in granulated lactose, pressed with a pressure of about 170 MPa.

Consequently, the density gradient in axial direction at a bulk density of 1.317 $g/cm^{-3}$ is not greater than 0.05% and the density gradient in radial direction is not greater than 0.3%, wherein the minimum density is found approximately in the middle of the wall thickness of the ring tablet. With these properties, a drug supply fabricated by this method is optimally suited for an aerosol generator as described in the above-referenced WO 93/24165, since with this device, the particles are removed from the drug supply by a face cutter operating in axial direction. Consequently, a very tightly distributed, identical concentric density distribution which does not affect the quality or quantity of the aerosol, is encountered across the entire usage region. It is also important that the pressing operation can be carried out without any auxiliary pressing means. For example, the ring-shaped drug supply according to the invention may be simply affixed to the tablet holder of an aerosol generator with cyanoacrylate glue.

It should be restated that the data discussed above and the materials of the drug supply are only provided as examples and that the present invention can be applied to a variety of drug materials and mixtures, respectively. The term drug here includes any pharmaceutical composition.

What is claimed is:

1. A solidified drug supply for making inhalable drug particles through a metering device including a removal means for abrading the solidified drug supply, said drug supply comprising a solidified body of medicament having a substantially uniform radial density formed by applying a radial pressing force from outside in a direction toward a core positioned centrally in the solidified body.

2. The drug supply of claim 1 wherein the pressing force is applied in a direction essentially perpendicular to the direction of removal.

3. The drug supply of claim 1 wherein the solidified body has a circular ring shaped cross section.

4. The drug supply of claim 1 wherein the solidified body is fabricated from a granulated carrier material-active ingredient mixture.

5. The drug supply of claim 1 wherein the solidified body is fabricated from a granulated carrier material-active ingredient mixture at a pressing force between 50 and 500 MPa.

6. The drug supply of claim 1 wherein the solidified body exhibits a radial density gradient of no more than 0.3% perpendicular to the direction of abrasion.

7. The drug supply of claim 1 wherein the solidified body exhibits a radial density gradient of no more than 0.05% in the direction of abrasion.

8. A process of making a solidified drug supply for producing inhalable drug particles by means of a metering device including a removal unit for abrading the drug supply, said process comprising the step of applying from outside a pressing force onto a medicament material in a direction toward a core positioned centrally in the medicament material resulting in a substantially uniform radial density of the solidified drug supply.

9. The process of claim 8, and further comprising the step of pre-shaping the medicament material into a body of medicament prior to said force applying step.

10. The process of claim 9 wherein the body of medicament is pre-shaped in the form of an annulus.

11. The process of claim 8, and further comprising the step of removing the core after the force applying step.

12. The process of claim 9 wherein the body of medicament is made from a rod-shaped body by separating a piece of suitable length in a direction perpendicular to a longitudinal extent of the rod-shaped body.

13. Apparatus for making a solidified drug supply, comprising:

a press having at least two stationary plates in spaced-apart and parallel disposition and a flexible ram, said plates and said ram having inner surfaces oriented perpendicular to one another as to form a medicament material receiving chamber;

a core positioned centrally in the chamber;

a pressure source for supplying a medium under pressure; and a pressure-transmitting means positioned at a core-distal side of the ram and acted upon by the medium under pressure to move the ram in a direction of a core, thereby compacting the medicament material.

14. The apparatus of claim 13 wherein the pressure-transmitting means is a flexible membrane which slides radially inwardly on confronting end faces of the plates, thereby ensuring application of only a radial pressing force onto the medicament material.

15. The process of claim 8 wherein the pressing force has a same magnitude across the entire outside surface of the medicament material.

* * * * *